US006300101B1

(12) United States Patent
Sadziene et al.

(10) Patent No.: US 6,300,101 B1
(45) Date of Patent: Oct. 9, 2001

(54) METHODS AND COMPOSITIONS INCLUDING A 13KD B. BURGDORFERI PROTEIN

(75) Inventors: Ariadna Sadziene; Alan G. Barbour, both of San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/264,036

(22) Filed: Jun. 22, 1994

Related U.S. Application Data (63) Continuation-in-part of application No. 08/079,601, filed on Jun. 22, 1993, now Pat. No. 5,523,089, which is a continuation of application No. 07/924,798, filed on Aug. 6, 1992, now abandoned, which is a continuation of application No. 07/422,881, filed on Oct. 18, 1989, now abandoned.

(30) Foreign Application Priority Data

Oct. 24, 1988 (DK) .................................................. 5902/88

(51) Int. Cl.[7] ........................... C12P 21/06; A61K 39/02; C07K 1/00

(52) U.S. Cl. ..................... 435/69.3; 424/234.1; 530/402; 530/825

(58) Field of Search ......................... 424/234.1; 530/402, 530/825; 435/69.3

(56) References Cited

U.S. PATENT DOCUMENTS

| | | | |
|---|---|---|---|
| 4,801,540 | 1/1989 | Hiatt et al. | 435/172.3 |
| 5,155,022 | 10/1992 | Naqui et al. | 435/7.32 |
| 5,217,874 | 6/1993 | Guadagno et al. | 435/28 |
| 5,246,844 | 9/1993 | Norris et al. | 435/172.3 |

FOREIGN PATENT DOCUMENTS

| | | |
|---|---|---|
| WO 90/04411 | 5/1990 | (WO) . |
| 9004411 * | 5/1990 | (WO) . |

OTHER PUBLICATIONS

Karlsson (*J. Clin. Microbiol., 28*(9) :2148–2150, 1990).
Wallich et al. (*Infect. Immun., 58*(6) :1711–1719, 1990).
Simpson et al. (*J. Clin. Microbiol., 28*(6) :1329–1337, 1990).
Cluss and Boothby (*Infect. Immun., 58*(4) :1038–1042, 1990).
Brandt et al. (*Infect. Immun., 58*(4) :983–991, 1990).
Schutzer et al. (*Lancet, 335*312–315, 1990).
Jiang et al. (*J. Immunol., 144*(1) :284–289, 1990).
Borenstein et al. (*Ann. Meet. Am. Soc. Microbiol., 90*(0) :46, Abstract #B–116, 1990).
Norris et al. (*Ann. Meet. Am. Soc. Microbiol., 90*(0) :103, Abstract #D–135, 1990).
Luft et al. (*Infect. Immun., 57*(11) :3637–3645, 1989).
Steere (*New Eng. J. Med., 321*(9) :586–596, 1989).
Cunningham et al. (*Ann. N.Y. Acad. Sci., 539*:376–378, 1988).*
Grodzicki and Steere (*J. Infect. Dis., 157*:(4) :790–797, 1988).*
Barbour (*Yale J. Biomed., 57*:581–586, 1984).*
Dialog Search Report.*
Howe et al., "Organization of Genes Encoding Two Outer Membrane Proteins of the Lyme Disease Agent *Borrelia burgdorferi* within a Single Transcriptional Unit:", Infection and Immunity, 54:207–212, 1986.*
Sadziene, et al., "An OSP–Less Mutant of *Borrelia Burgdorferi Sensu Lato*: Biological, Immunological and Molecular Characterization", International Conference on Lyme Borreliosis, Bologna, Italy, Jun. 19–22, 1994.*
Berg et al., "The Laboratory Diagnosis of Lyme Disease," *Arch Dermatol*, 127:866–870, Jun. 1991.
Kalish, Robert, M.D., "Lyme Disease," *Rheumatic Disease Clinics of North America*, 19:(2)399–426, May 1993.
Katona et al., "Purification and Immunological Characterization of a Major Low–Molecular–Weight Lipoprotein from *Borrelia burgdorferi*, " *Infection and Immunity*, 4995–5003, Dec. 1992.

(List continued on next page.)

*Primary Examiner*—James C. Housel
*Assistant Examiner*—Rodney P. Swartz
(74) *Attorney, Agent, or Firm*—Frommer Lawrence & Haug LLP; Thomas J. Kowalski (57) ABSTRACT

All *Borrelia burgdorferi* sensu lato isolates characterized to date have one or a combination of several major outer surface proteins (Osp). Mutants of *B. burgdorferi* lacking Osp proteins were selected with polyclonal or monoclonal antibodies at a frequency of $10^{-6}$ to $10^{-5}$. One mutant that lacked OspA, B, C and D was further characterized in the present study. It was distinguished from the OspA$^+$B$^+$ cells by its (i) auto-aggregation and slower growth rate, (ii) decreased plating efficiency on solid medium, (iii) serum- and complement-sensitivity, and (iv) diminished capacity to adhere to human umbilical vein endothelial cells. The Osp-less mutant was unable to evoke a detectable immune response after intradermal live cell immunization even though mutant survived in the skin the same duration as wild-type cells. Polyclonal mouse serum raised against Osp-less cells inhibited growth of the mutant but not of wild-type cells, an indication that other antigens are present on the surface of the Osp-less mutant. Two different classes, A and B, of monoclonal antibodies (mAb) with growth inhibiting properties for mutant cells were produced. Class A mAbs bound to 13 kDa surface proteins of *B. burgdorferi* sensu stricto and of *B. afzelii*. The minimum inhibitory concentration of the Fab fragment of one mAb of this class was 0.2 μg/ml. Class B mAbs did not bind by Western Blot to *B. burgdorferi* cells but reacted with cells in an unfixed cell immunofluorescence assay and growth inhibition assay. These studies revealed hitherto unknown functional aspects of Osp proteins, notably serum-resistance, and indicated that in the absence of Osp proteins other antigens are expressed or become accessible at the cell's surface.

10 Claims, 5 Drawing Sheets

OTHER PUBLICATIONS

Sambri et al., "Immunological characterization of a low molecular mass polypeptidic antigen of *Borrelia burgdorferi*," *FEMS Microbiology Immunology*, 76:345–350, 1991.

Szczepanski et al., "Lyme Borreliosis: Host Response to *Borrelia burgdorferi*," *Microbiological Reviews*, Mar. 21–34, Mar. 1991.

Wilske et al., "Antigenic variation and strain heterogeneity in *Borrelia* spp.," *Res. Microbiol.*, 143:583–596, 1992.

Sambri et al FEMS Microbiol. Immunol 76:345–350, 1991.*

Katona et al Infect Immun 60(12): 4995–5003, 1992.*

Berg et al Arch Dermatol 127:866–870, 1991.*

Kalish et al Rheum. Dis. Clin. North Am 19(2):399–426, 1993.*

Wilske et al Res Microbiol 143:583–596, 1992.*

Szczepanski et al Microbiol Rev 55(1): 21–34, 1991.*

* cited by examiner

PHOTOMICROGRAPHS
DIRECT IMMUNOFLUORESCENCE

METHODS AND COMPOSITIONS INCLUDING A 13KD *B. BURGDORFERI* PROTEIN

This application is a continuation-in-part of application Ser. No. 08/079,601, filed Jun. 22, 1993, now U.S. Pat. No. 5,523,089, which is a continuation of U.S. application Ser. No. 07/924,798, filed Aug. 6, 1992, now abandoned, which is a continuation of U.S. application Ser. No. 07/422,881, filed Oct. 18, 1989, now abandoned, claiming priority from Danish application 5902/88, filed Oct. 24, 1988.

BACKGROUND OF THE INVENTION

Lyme disease is a complex, multisystemic illness caused by at least three genomic species of the spirochete *Borrelia burgdorferi* sensu lato (reviewed in Barbour and Fish, 1993). Virtually all North American isolates have been classified as *B. burgdorferi* sensu stricto (Baranton et al., 1992; Boerlin et al., 1992; Welsh et al., 1992). European isolates also include two other genomic species, *B. garinii* and *B. afzelii* (Baranton et al., 1992; Canica et al., 1993). The clinical features and epidemiology of Lyme disease have been well characterized (reviewed review in Barbour and Fish, 1993). Comparatively less, however, is known about the pathogenic features of Lyme disease borrelias and immunopathological responses to them in the host.

Ignorance of precise mechanisms of Lyme disease pathogenesis is partly attributable to the paucity of basic information about all spirochetes. The spirochete cell is unique in several aspects (Holt, 1978). One of the features of borrelia is the abundance of one or several lipoproteins in the outer cell membrane (Bergstrom et al., 1989; Brandt et al., 1990; Brusca et al., 1991; Howe et al., 1985; Norris et al., 1992). Much has been learned about immunogenicity, as well as biochemical and genetic aspects, of these lipoproteins in Lyme disease and relapsing fever borrelias (Barbour, 1993; Bergstrom et al., 1989; Brandt et al., 1990; Johnson et al., 1992; Kitten and Barbour, 1990; Meier et al., 1985; Wilske et al., 1993).

The lipoproteins OspA and OspB are major contributors to antigenic distinctness of Lyme disease borrelias (Barbour and Fish, 1993). Both OspA and OspB are co-transcribed from a single operon located on linear plasmid of 49 kb in *B. burgdorferi* sensu stricto (Bergstrom et al., 1989). Many of European and some North American *B. burgdorferi* sensu lato strains express a third immunodominant major protein, OspC (Wilske et al., 1993). Another protein of this group, OspD, has been also reported (Norris et al., 1992). Proteins called "OspE" and "OspF" have been reported, but their surface exposure and location in the outer membrane have not been established (Lam et al., 1994).

OspA and OspB may contribute to the spirochete's ability to adhere to or invade host cells (Benach et al., 1988; Comstock et al., 1992; Thomas and Comstock, 1989). It has been suggested that OspA may affect the chemotactic response of human neutrophils in vitro (Benach et al., 1988). Mitogenic and cytokine-stimulatory properties of OspA and OspB have been also shown (Ma and Weis, 1993). It was found that reduced size and amounts of OspB was associated with lowered infectivity (Sadziene et al., 1993A). The findings of Cadavid et al. indicated that differences in invasive properties and tissues tropism between serotypes of related spirochete *Borrelia turicatae*, a relapsing fever agent, may be determined by the expression of a single surface protein that is analogous to Osp proteins of *B. burgdorferi* (Cadavid et al., 1994).

These studies of function of Osp proteins, however, are still limited in number. More information is needed regarding the function of these proteins, in particular their roles in infectivity and their contributions to the microorganism's ability to survive in the host. One approach to obtain these insights is selection and characterization of mutants with altered surface lipoproteins. There were several compelling reasons for studying *B. burgdorferi* cells that lacked all known Osp proteins (Sadziene et al., 1992, Sadziene et al., 1993B). First the morphology and function of the Osp-less mutant were characterized to determine whether borrelias lacking OspA, B, C, and D would be altered in such functional properties, as (i) generation time, (ii) ability to form colonies on solid medium, (iii) adherence to cells, (iv) serum and complement sensitivity, (v) potential to evoke immune response after intradermal live cell inoculation, and (vi) ability to survive in the skin. Among pathogenic borrelias the role of surface lipoproteins in these respects have not yet been reported.

Another intriguing aspect was the immunological characterization of the Osp-less mutant. There have been several studies describing low molecular weight lipoproteins that have not been identified as Osps. Katona et al. showed the presence of a major low-molecular-weight lipoprotein specific for *B. burgdorferi* and raised the possibility that it was a borrelial equivalent of Braun’s lipoprotein (Katona et al., 1992). Another study reported an immunogenic 14 kDa surface protein of *B. burgdorferi* recognized by sera from Lyme disease patients (Sambri et al., 1991). These findings encouraged us to determine whether other proteins are present on the surface in the absence of Osp proteins.

BRIEF DESCRIPTION OF THE DRAWINGS

FIG. 1A. Phase contrast photomicrograph of aggregation of *B. burgdorferi* 313 by monoclonal antibodies. 4+ aggregation (see Methods) by class A antibody.

FIG. 1B. Phase contrast photomicrograph of aggregation of *B. burgdorferi* 313 by monoclonal antibodies. 3+ aggregation by class B antibody. Bar, 1.0 μm.

FIG. 2. Coomassie blue-stained polyacrylamide gel (CB) and Western blot analysis (WB) of whole-cell lysates of *B. burgdorferi* isolates B31, B311, B312, B313, and B314 with either monoclonal antibody 15G6 and 7D4. The acrylamide concentration was 17%. The molecular size standards (×1000) were ovalbumin, carbonic anhydrase, β-lactoglobulin, lysozyme, and bovine trypsin inhibitor.

FIG. 3: FIGS. 3A, 3B:

FIG. 3A. Western blot analysis with antibody 15G6. *B. burgdorferi* B311 and B313, *B. afzelii* ACAI, *B. garinii* IP90 and *B. hermsii* Bh33 were probed with the antibody 15G6 mAb.

FIG. 3B. B313 cells treated (+) or untreated (−) with proteinase K (PK). The molecular size standards (×1000) were carbonic anhydrase, β-lactoglobulin, lysozyme, and bovine trypsin inhibitor.

FIG. 4: FIGS. 4A, 4B, 4C:

FIGS. 4A, 4B, 4C. Binding of fluorescein-conjugated monoclonal antibody 15G6 to *B. burgdorferi* B313. FIG. 4A and FIG. 4B show direct immunofluorescence of unfixed cells in suspension for 3 min (left) and 15 min (right). FIG. 4B shows phase contrast photomicrograph of aggregates and membrane blebs (arrow head). Bar, 10 μm.

FIG. 5: FIGS. 5A, 5B, 5C, 5D:

FIG. 5A. Phase contrast photomicrographs FIGS. 5A,5B and direct immunofluorescence FIGS. 5C,5D of unfixed *B. burgdorferi* in suspension.

FIGS. 5A and 5C show B313 cells with fluorescein-conjugated antibody 15G6.

DETAILED DESCRIPTION OF THE PREFERRED EMBODIMENTS

MATERIALS AND METHODS

Strains and Culture Conditions

B. burgdorferi sensu stricto mutants were of the B31 (ATCC 35210) lineage (Table 1). The Osp phenotypes and plasmid contents of noninfectious derivatives B311, B312, B313 and B314 were described previously under these or other designations (Barbour, 1984; Barbour and Garon, 1987; Hinnebusch and Barbour, 1992; Sadziene et al., 1993B). Populations that were passed in medium not more than 10 times were considered low passage isolates. The low passage, infectious progenitor for this lineage retained the original strain designation, B31 (Burgdorferi et al., 1982). With the exception of B31, all cells of this lineage were grown from single cell clones. In some experiments other strains were used: HB19 (Barbour et al., 1983; Steere et al., 1983) and Sh.2 (Schwan et al., 1988), both of which are B. burgdorferi sensu stricto, B. afzelii strain ACAI (Boerlin et al., 1992) and B. garinii strain Ip90 (Baranton et al., 1992; Boerlin et al., 1992) (Table 1). B. hermsii HS1 serotype 33 (ATCC 35209; Barbour et al., 1982) was abbreviated to Bh33. Borrelias were grown in BSK II medium and harvested by methods described previously (Barbour, 1984; Barbour et al., 1983). When culturing tissues from animals, rifampicin (50 μg/ml), phosphomycin (100 μg/ml) and, for skin samples, additionally amphotericin (25 μg/ml) were added to the medium. Cells were counted in a Petroff-Hauser chamber by phase-contrast microscopy. In some studies borrelias were also grown on solid BSK II medium as described (Hinnebusch and Barbour, 1992; Sadziene et al., 1992). To estimate growth rate, borrelias at an initial concentration of $2 \times 10^6$ cells/ml, were grown in tightly capped, 13×100-mm polystyrene culture tubes (Falcon Labware, Lincoln Park, N.J.) containing 6 ml of medium. Growth at 34° C. in 1% $CO_2$ atmosphere was monitored visually and by cell counts every 12 h for 3 d. The amount of total cellular protein in the final cell pellet was determined with Bradford reagent (Bio-Rad Laboratories, Richmond, Calif., (Barbour et al., 1983). The microscopic aggregation of borrelias alone or in the presence of antibodies was graded according to the following scale: 0, single cells with less than 10% of the cells in clumps of 2–10 cells; 1+, 10–50% of cells in clumps of 2–10, 2+, 10–50% of cells in clumps of 11–100; 3+, >50% of cells in clumps of 11–100; and 4+, >50% of cells in clumps of >100.

TABLE 1

ISOLATES OF B. BURGDORFERI SENSU LATO USED IN THE STUDY AND THEIR OSP PROFILE

| Genomic species | Isolate | OspA | OspB | OspC | OspD | Reference |
|---|---|---|---|---|---|---|
| B. burgdorferi | B31 | + | + | − | + | Burgdorfer et al. 1982; Sadziene et al. 1993B |
|  | B311 | + | + | − | − | Barbour, 1984; Barbour and Garon, 1987; Sadziene et al, 1993B. |
|  | B312 | + | + | + | − | Hinnebusch and Barbour, 1992; Sadziene et al, 1993B. |
|  | B313 | − | − | − | − | Sadziene et al, 1992, 1993b. |
|  | B314 | − | − | + | − | Sadziene et al, 1993B. |
|  | HB19 | + | + | + | + | Barbour et al, 1983.; Steere et al., 1983 |
|  | Sh.2 | + | + | + | − | Schwan et al., 1988 |
| B. afzelii | ACAI | + | + | + | − | Boerlin et al., 1992 |
| B. garinii | IP90 | + | + | + | − | Baranton et al., 1992; Boerlin et al., 1992 |

[a]Osp profile was determined by Western blot analysis.

Antisera and Monoclonal Antibodies (mAbs)

The origins of the OspA-specific mAb H5332 (Barbour et al., 1983), OspB-specific mAb H6831 (Barbour et al., 1984) and Vmp33-specific mAb H4825 (Barbour et al., 1984) have been given. Monoclonal antibody H9724 binds to native and denatured flagellins of different Borrelia species (Barbour et al., 1986). These antibodies are IgG subclass 2a (IgG2a).

Additional polyclonal and monoclonal antibodies were produced for this study. Female, 6–8 week old BALB/c mice (Jackson Laboratory, Bar Harbor, Ma.) were used. Freshly-harvested borrelias were washed with and resuspended in PBS, pH 7.0. The total cellular protein in the suspension was estimated with Bradford reagent and adjusted with PBS for a total protein concentration of 200 μg/ml. 0.5 ml of antigen-suspension was emulsified in 0.5 ml of complete Freund's adjuvant (CFA; Sigma Chemical Co., St. Louis, Mo.), and 200 μl of emulsion was administered as six subcutaneous injections at day 0. Control mice received a 200 μl emulsion of equal parts of CFA and PBS alone. The total dose per mouse was 20 μg protein. After 4 weeks mice were boosted with the same dose. Mice were bled by eye sinus puncture 10 days after the boost. After collection, sera were evaluated by ELISA and GIA. On day 52, the mice received intravenously $2 \times 10^8$ viable borrelias in 100 μl of PBS. Fusion of mouse splenocytes with NS1 myeloma cells were performed on day 56 by a modification of the previous method (Oi and Herzenberg, 1980). Undiluted hybridoma supernatant fluids without antibiotics were screened by wet ELISA, unfixed cell IFA and Western Blot techniques. Those fluids that were positive by either one of these methods were then evaluated by GIA. For GIA hybridoma supernatant fluids were dialyzed against PBS, pH 7.0 and concentrated with Centriprep®-10 (Amicon, Beverly, Mass.) cartridges. The isotypes of antibodies were determined using a commercial kit (Immunotype™; Sigma Chemical Co., St. Louis, Mo.). Ascitic fluids from hybridomas were produced as described (Sadizene et al., 1994).

Purified mAbs and univalent Fab fragments were prepared from hybridoma supernatants essentially as described (Sadziene et al., 1993C). Briefly, hybridoma supernatants were concentrated using an Amicon 8200 membrane concentrator with a Diaflo® YM30 ultrafiltration membrane (Amicon) under 50 psi $N_2$. Purified mabs were obtained by Protein A-sepharose column chromatography. Univalent Fab fragments were prepared using the Immunopure® Fab Preparation kit (Pierce Chemical Co.) by cleaving the purified antibodies with papain, retaining intact immunoglobulin and Fc fragments on a protein A-sepharose column, and dialyzing the void volume of the column against PBS, pH 7.0. Purified mAbs and Fab fragments were concentrated with Centriprep®-10 (Amicon). Protein concentrations were determined by UV spectrophotometry at 280 nm. Purified whole IgG and Fab fragments were analyzed by SDS-PAGE. Reactivities of purified mAbs and Fab fragments were confirmed by direct and indirect immunofluorescence assay, Western blot and GIA.

ELISA

The method for ELISA was essentially as described previously (Sadziene et al., 1991). For this "dry" ELISA borrelias at a total protein concentration of 1.4 μg/ml in phosphate-buffered saline (PBS), pH 7.0 were dried onto polystyrene 96-well microtiter plates at 37° C. for 18 h. For a "wet" ELISA borrelias at a total protein concentration of 3 μg/ml in 15 mM $Na_2CO_3$-35 mM $NaHCO_3$ buffer, pH 9.6 were coated onto plates at 4° C. for 24 h. After blocking for 1 h at 37° C. with 1 (wt/vol) dried nonfat milk in PBS (milk/PBS) and washing with PBS alone, twofold dilutions of antibody in milk/PBS were added. The plates were incubated for 2 h at 37° C. and washed with PBS. Bound antibody was measured using alkaline phosphatase-conjugated goat anti-mouse IgG (Zymed). The substrate was p-nitrophenyl phosphate (Sigma). Absorbance values were recorded at 490 nm on a model 580 ELISA reader (Dynatech Laboratories, Chantily, Va.); wells with values $\geq 0.2$ were considered positive.

Immunofluorescence Assays

Indirect immunofluorescence assay (IFA) of fixed, dried cells was performed as described (Barbour et al., 1982; Barbour et al., 1983). Harvested, fresh borrelias were washed with RPMI 1640 medium, mixed with a suspension of washed rat erythrocytes in 50% RPMI 1640-50% fetal calf serum, and a thin smear of the suspension was coated on the slides. Slides were fixed in methanol, air dried, and kept in a dessicator at −20° C. until use.

Binding of mAb to unfixed live spirochetes was assessed by a modification of the described procedure (Barbour et al., 1983). $10^7$ borrelias were washed with 2% (wt/vol) BSA in PBS/Mg (PBS/Mg/BSA) and then resuspended in 0.5 ml of undiluted hybridoma culture supernatant or 0.5 ml of PBS/Mg/BSA containing the mAb of interest. The cell mixture was incubated at room temperature with gentle rotation for 60 min. The cells were centrifuged, washed twice with PBS/Mg/BSA, resuspended in 30 μl volume of PBS/Mg/BSA with 20 μg/ml of anti-mouse Ig-fluorescein F(ab')$_2$ fragment (Boehringer-Mannheim, Indianapolis, Ind.) and incubated for 30 min under the same conditions. Before microscopic evaluation the volume of the cell suspension was adjusted to 300 μl with PBS/Mg/BSA.

For direct IFA purified mAbs and their Fab fragments were conjugated with fluorescein isothiocyanate (QuickTag FITC Conjugation Kit; Boehringer-Mannheim). Fractions containing the antibody-fluorescein conjugate were mixed together, dialyzed in the dark against PBS for 24 h, and concentrated with a Centriprep®-10 (Amicon, Beverly, Mass.). $10^7$ borrelias in log-phase growth were resuspended in RPMI 1640 medium with 10–100 μg/ml of antibody-fluorescein conjugate and examined for fluorescence at 3, 15, 30, 60, and 360 min.

Growth Inhibition Assays

The growth inhibition assay (GIA) was described previously (Sadziene et al., 1993C). Briefly, to a 100 μl volume of BSK II containing $2 \times 10^6$ borrelias was added an equal volume of heat-activated (56° C. for 30 min) mAb or polyclonal antiserum, serially diluted two-fold in BSK II. To evaluate the susceptibility of borrelias to fresh, nonimmune serum, the same growth inhibition technique was applied using pooled unheated serum from C3H/HeN mice (Taconic, Germantown, N.Y.). Blood was drawn on ice, separated from red blood cell clot, and immediately frozen at −135° C. Heat-inactivated serum from the same mice served as a control. To determine the susceptibility of borrelias to complement, unheated or heated (56° C. for 30 min) guinea pig complement (Diamedix, Miami, Fla.) was added to each well at an activity ranging from 6 to 1 hemolytic unit (HU; $CH_{50}$) per well. In some experiments, 2 HU of unheated guinea pig complement were added to each well for a final concentration of 10 HU/ml of medium after addition of antibody.

The incubations were performed in flat-bottomed, 96-well, polystyrene microtiter plates, covered by adhesive, clear plastic seals (Sensititre Microbiologic Systems, Westlake, Ohio) and were carried out for 72 h at 34° C. in a 1% $CO_2$ atmosphere. Growth in the wells was monitored visually for changes in the color of the phenol red indicator and by phase contrast microscopy of wet-mounts of culture samples. A pink color of the indicator after incubation represented at least 20-fold fewer cells in these wells than in wells that were yellow. The minimal inhibitory concentration (MIC) was the lowest concentration of mAb that produced pink instead of yellow wells (Sadziene et al., 1993C). All growth inhibition studies were performed at least twice.

Electrophoresis and Western Blot Analysis

Whole-cell lysates were subjected to sodium dodecyl sulfate-polyacrylamide gel electrophoresis (SDS-PAGE) with 15% or 17% acrylamide as described previously (Barbour, 1984; Barbour et al., 1982). In some experiments, cleavage of surface-exposed proteins of intact borrelias with proteinase K (Boehringer-Mannheim) was carried out (Sadziene et al., 1992). For this study 490 μl of a suspension containing $5 \times 10^8$ cells in PBS/Mg was mixed with 10 μl of proteinase K solution (20 mg/ml of water) and incubated for 40 min at 22° C. The reaction was stopped by the addition of phenylmethylsulfonyl fluoride.

For Western blot analysis, proteins were transferred to nitrocellulose membranes, which were then blocked with 3% (wt/vol) dried nonfat milk in 10 mM Tris-HCl (pH 7.4)-150 mM NaCl (milk/TS) for 2 h as described before (Oi and Herzenberg, 1980). After a wash in milk/TS, membranes were incubated with mAb ascitic fluid diluted 1:50 or 1:100 in milk/TS or hybridoma supernatant fluid diluted 1:5 or 1:10 in milk/TS. Alkaline phosphatase=conjugated recombinant protein A/G (Immunopure; Pierce Chemical Co., Rockford, Ill.) served as the second ligand. The blots were developed with nitro-blue tetrazolium chloride and 5-bromo-4-chloro-3-indolylphosphatase p-toluidine salt (Pierce, Rockford, Ill.).

Adherence Assay

An assay for adherence of intrinsically-labeled borrelias to human umbilical vein endothelium (HUVE) cells was carried out essentially as described (Thomas and Comstock, 1989). Briefly, borrelias were intrinsically radiolabeled with [$^{35}$S]-methionine, washed with PBS and resuspended to a density of $1.7 \times 10^8$ cells per ml in Medium 199 with 20% fetal calf serum. 300 μl aliquots of radiolabeled spirochetes were added to confluent HUVE cell monolayers grown in 24-well plates. After a 4 hr incubation at 4° C., monolayers with associated organisms were washed, solubilized, mixed with scintillation cocktail (Universol ES; ICN Pharmaceuticals, Irvine, Calif.), and counted by scintillation. The assay was done with triplicate samples and performed twice. Differences between borrelia populations in adhesion were analyzed by Student's t test.

Experiments in Mice

Six-to-eight week old, female C3H/HeN mice (Taconic, Germantown, N.Y.) were used. Borrelias were counted and diluted in BSK II to give the desired inoculum. For live cell immunization, 10 $\mu$l of cells in BSK II medium was transferred to 900 $\mu$l of sterile PBS solution immediately prior to immunization. 100 $\mu$l of this suspension then was inoculated intradermally in the abdomen at day 0. As a control, 100 $\mu$l of 0.1X BSK II in PBS was used. On day 24 mice were bled from the tail vein, and their sera were examined by ELISA and GIA. Mice were challenged on day 28 at the base of the tail with $10^4$ of B. burgdorferi strain Sh.2 (Sadziene et al., 1993A). Mice were euthanized 14 d following infection. Plasma (0.5 ml) obtained from citrated blood, the whole bladder, macerated heart, and cross-cuttings of both tibiotarsal joints were added to BSK II medium and cultured at 34° C. Cultures were examined for the presence of motile spirochetes by phase-contrast microscopy at days 7 and 14 of cultivation; they were scored as negative when no motile spirochetes were seen in forty 400x fields. For evaluation of borrelia survival in skin, borrelias were diluted in 1X BSK II. The abdominal skin was shaved, and $10^7$ borrelia cells were injected intradermally at 3 or 4 separate locations. Mice were sacrificed at 0.25, 0.5, 2, 6, 9, 12, 18 and 24 h after injection and samples of skin from the injection sites were immediately cultured in BSK II medium at 34° C.

RESULTS

Isolate B313 of the B31 lineage of B. burgdorferi lacked OspA, B, C, D (Table 1; Sadziene et al., 1992; Sadziene et al., 1993B). This mutant was selected from a clonal population of B31 under the selective pressure of an anti-OspA mAb. Isolate B311's Osp profile was OspA$^+$B$^+$C$^-$D$^-$. Mutants that lack both OspA and OspB were selected with polyclonal or monoclonal antibodies directed against B. burgdorferi at a frequency of $10^6$–$10^{-5}$ (Sadziene et al., 1992). The genetic basis for the Osp-less phenotype was loss of a 38 kb and 49 kb linear plasmids and retention of a 16 kb plasmid (Norris et al., 1992; Sadziene et al., 1992; Sadziene et al., 1993B).

Growth Rate

Osp-less mutant B313 was easily distinguishable from B311, as well as from other high-passage, Osp-bearing isolates of the B31 lineage, in broth culture by its tendency to form microscopic aggregates. B313 cultures had aggregation scores of 1+ or 2+, whereas B311 had a score of 0. Another observed difference was the decreased ability of B313 cells to turn the phenol red indicator yellow in the BSK II, even when the culture reached stationary phase. One possible explanation for this is that metabolic activity of the Osp-less mutant was lower than that of wild-type borrelias. Alternatively, the OspA$^-$ OspB$^-$ mutant may have a slower rate of growth than its parent B311 and, consequently, does not reach the same cell densities as wild-type borrelias at a particular time point. To examine these possibilities the growth rates of B311 and B313 were determined and the amount of borrelia protein in the final cell pellet was measured.

B311 and B313 cells were grown until stationary phase, that is, when no further growth occurred, was reached. Cell counts were determined every 12 h in triplicate, and the $\log_{10}$ of mean cell counts were plotted against time. At stationary phase B311 cultures had a cell density of 1.5–2.0× $10^8$ cells/ml and B313 cultures had a cell density of 4–5× $10^7$, fourfold lower. Protein concentrations in the final B311 and B313 cell pellets were 0.65 mg and 0.16 mg, respectively, a finding consistent with the cell counts. The mean generation time (± standard error of the mean) of B311 cells was 6.6±0.1 h; the values for B313 cells were 9.5±0.2 h, 50% slower. These findings indicated that the Osp-less cells both grew more slowly and achieved a lower final cell mass than did their Osp-bearing counterparts.

Plating Efficiency

Another biological characteristic of the Osp-less mutant was also evaluated, namely, its ability to grow as a colony on solid medium. Current procedures for cultivation of different low and high passage B. burgdorferi on solid medium yield efficiencies of plating between 50 and 100% (Hinnebusch and Barbour, 1992; Sadziene et al., 1993A; Sadziene et al., 1992). In previous studies it was found that other antibody-resistant variant populations of the B31 lineage could be plated with the same high efficiency (Sadziene et al., 1992). An exception was the very low plating efficiency of mutant B314 (Table 1), which lacks all linear plasmids and has an OspA$^-$B$^-$C$^+$D$^-$ phenotype (Sadziene et al., 1993B). These data suggested that mutants with Osp$^-$ phenotype might also have a lesser ability to form colonies.

This study was performed twice, each time plating in triplicate $10^1$–$10^6$ borrelias per plate. B311 cells grew as colonies with the expected plating efficiency of 50%. The efficiency of B313 plating was 0.01%, more than a thousand-fold lower than for B311 cells under the same conditions. Of three arbitrarily-chosen colonies of B311 that grew in broth medium and were then subjected to SDS-PAGE, all retained the Osp-less phenotype.

Adherence to Endothelial Cells

Adherence of radiolabeled B. burgdorferi B311 and B313 cells to HUVE cell monolayers was measured after 4 h at 4° C. At this temperature borrelias do not detectably enter endothelial cells and adherence of cells becomes maximal by 4 h (Comstock and Thomas, 1989). The assay was repeated twice. Results of two studies are shown in Table 2. The ability of Osp-less cells to adhere HUVE monolayer both times was only half that of wild-type borrelias, a difference that was significant (P<0.001).

Serum and Complement Sensitivity

Wild-type B. burgdorferi is resistant to the nonspecific bactericidal activity of nonimmune serum, in spite of classical and alternative complement pathway activation (Kochi and Johnson, 1987). It was determined whether or not the borrelias' ability to resist the nonspecific bactericidal effects of complement might be attributable to Osp proteins. Accordingly, B311 cells and the Osp-less mutant were first exposed to two-fold serially diluted fresh, naive mouse serum in a GIA. Heat-inactivated serum was applied in the same assay in parallel. As expected, B311 cells were resistant to the nonimmune serum; no growth inhibitory effect on the cells was observed at the lowest serum dilution of 1:8. In contrast, the minimum inhibitory titer of nonimmune serum against Osp-less borrelias was 1:64. In wells with inhibited growth the B313 cells were nonmotile and had large

TABLE 2

ADHERENCE TO HUVE CELLS BY B311 AND B313

| Experiment[a] | Cell population | Adherence[b] Mean cpm adhered ± SEM[c] | Mean % of inoculum adhered[d] |
|---|---|---|---|
| I | B311 | 14719 ± 134 | 5.0 |
|   | B313 | 7360 ± 36 | 2.5 |
| II | B311 | 13447 ± 92 | 5.7 |
|   | B313 | 6801 ± 83 | 2.9 |

[a]The specific activities of inocula for adherence assays in experiments I and II were $2.9 \times 10^5$ and $2.3 \times 10^5$ cpm, respectively.
[b]Measured following incubation for 4 h at 4° C.
[c]Radioactivity bound to host cells following incubation and washing, expressed as the mean of three samples.
[d]Differences between borrelia populations in adhesion were analyzed by a Student's t test ($P < 0.001$).

membrane blebs. When heat-inactivated serum was applied to either B311 or B313 cells, growth inhibition or these morphologic effects were not observed at a serum dilution 1:8. These findings suggested that complement affected the Osp-less cells.

To further evaluate the serum-susceptibility of the Osp-less mutant, the effect of different activities of guinea pig complement on B311 and B313 cells was compared. The dose of applied complement varied between 1–6 HU per well, and, as a control, the same doses of heat-inactivated complement were used. The study was performed twice. Whereas heat-inactivated guinea pig complement had no growth inhibitory effect on either isolate at the doses of 6 HU or less per well, there were substantial differences in the effect of unheated complement on B313 and B311. As little as 1 HU of complement inhibited growth of B313; this represented an MIC of $\leq 5$ HU/ml. The corresponding MIC of unheated complement for B3311 cells was $\geq 25$ HU/ml.

The frequency of B313 cells surviving in the presence of complement was also estimated. Because of B313's poor growth on solid medium, the study was performed in 96-well microtiter plates (Sadziene et al., 1992). $5 \times 10^6$ of B311 or B313 cells were exposed to 3 HU/tube of guinea pig complement for 6 h. After this time cell suspensions were diluted to the concentration of complement less than 1 HU/tube and aliquoted in 200 $\mu$l volumes to individual microtiter plate wells at inocula ranging between $10^0$–$10^5$ cells per well. Cells that were exposed to heat-inactivated complement or no complement at all served as controls. The frequency of complement-resistant mutants of B313 was calculated using tables of the Poisson distribution to be $3$–$6 \times 10^{-5}$.

Of 11 complement-resistant B313 clones that were transferred to medium without complement, only 6 proliferated. When these 6 cultures were again exposed to 3 HU of complement, all were as susceptible as the parent population. This suggested that if some changes had occurred in the cell, they most likely represented a phenotypic change. When the 6 cultures derived from the resistant populations were examined by PAGE, there was no discernable difference between them and the control B313 protein profiles.

Survival of Borrelias in Skin

In the previous study it was shown that outer surface lipoproteins might have a role in protecting borrelias from one nonspecific host defense, namely, complement. Borrelias invade the host through the skin, being able to survive in it from a few days to years (Steere, 1989). Accordingly, it was evaluated whether Osp proteins might also protect borrelias from nonspecific resistance factors in the skin of the mouse., (e.g., different chemical substances from tissues with antibacterial activity, early inflammation factors, and phagocytic cells) (Boyd and Hoerl, 1986).

In a first step assessing these factors, it was determined how long B311 and B313 cells would survive in the skin after intradermal inoculation. The study was repeated twice. In total 8 to 12 separate skin locations were evaluated for spirochetal growth at the each time point. Mice were sacrificed at 0.25, 0.5, 2, 6,9,12, 18 and 24 h following inoculation, and full-depth skin biopsies were cultured. All cultures from up to 9 h were positive with both B311 and B313. In 12 h, 4 out of 8 and 5 out of 8 skin cultures were positive with B311 and B313 cells, respectively. None of the cultures from 18 and 24 h after inoculation was positive. These findings indicated that OspA and/or OspB might not benefit the borrelias' survival in the skin. To confirm that cells that survived in the skin retained the same phenotype, 6 randomly chosen cultures each of B311 and B313 were subjected to SDS-PAGE; all of the examined cells retained an unchanged protein profile.

Immunization by Intradermal Inoculation with Live Cells

The next study addressed whether live cells lacking known Osp lipoproteins were able to induce immune response in the skin and, if so, how that response differed from the one induced by osp-bearing cells. A rationale for this study was the fact that viable (but noninfectious) B. burgdorferi of strain HB19 (at single intradermal dose of $10^6$ live cells per mouse) were sufficient protect mice against challenge with 104 Sh.2 cells 4 weeks later (Sadziene and Barbour, 1994). This immunization dose was used with B311 and B313 cells in the present study. The immune responses of immunized and control mice were evaluated by ELISA and GIA with B311 and against the challenge strain, Sh.2.

As shown in Table 3 only immunization with cells expressing OspA and OspB, that is, B311, was effective in protecting all 5 mice from experimental infection with $10^4$ cells of the challenge strain. Osp-less B313 failed to elicit a protective immune response at a immunization dose of $10^6$ cells. All 5 mice that were immunized with live Osp-less mutant cells, as well as control mice injected with 0.1×BSK alone, became infected. Immune responses among the groups as evaluated by ELISA and GIA also differed substantially.

Whereas B311 cells evoked an immune response as assessed by ELISA and especially by GIA, the response to B313 cells in the same assays was similar to that of the control group. Western blot analysis with sera from mice immunized with B313 showed no response to proteins of B. burgdorferi, except for faint bands against flagellin (Sadziene et al., 1991). Inasmuch as both B313 and B311 appear to survive in the skin for the same time span, a possible explanation for these results of immunization was that Osp proteins are an important stimulus for the host immune system to recognize the spirochete.

Polyclonal Antisera to B311 and B313

The lack of an antibody response to B311 and other Osp-bearing cells by mice immunized with B313 might also be explained by the presence of unique antigens in B313 cells. According to this hypothesis, antibodies were produced in response to live cell immunization with B313 but they were directed against antigens found only in B313 cells. There have been reports indicating that B. burgdorferi has other surface proteinaceous antigens that those been defined as Osps (Brandt et al., 1990; Katona et al., 1992; Luft et al., 1989; Sambri et al., 1991; Simpson et al., 1991). These considerations suggested the possibility of non-Osp antigens' being present on the surface of the mutant cells.

TABLE 3

INTRADERMAL IMMUNIZATION AND PROTECTION OF MICE WITH LIVE B311 AND B313

| Immunogen[a] | Mouse No | ELISA[b] | GIA[c] | Experimental infection[d] |
|---|---|---|---|---|
| B311 | 1 | 256 | 1024 | 0/5 |
|  | 2 | 128 | 128 |  |
|  | 3 | 256 | 512 |  |
|  | 4 | 256 | 512 |  |
|  | 5 | 128 | 128 |  |
| B313 | 1 | 4 | <16 | 5/5 |
|  | 2 | 8 | <16 |  |
|  | 3 | 4 | <16 |  |
|  | 4 | 4 | <16 |  |
|  | 5 | 8 | <16 |  |
| Control[e] | 1 | 4 | <16 | 5/5 |
|  | 2 | 2 | <16 |  |
|  | 3 | 4 | <16 |  |
|  | 4 | 4 | <16 |  |
|  | 5 | 4 | <16 |  |

[a]$10^6$ cells were injected intradermally in the abdominal region of each mouse at day 0.
[b]Reciprocal ELISA titers of individual mouse sera against Sh.2 cells at day 24.
[c]Reciprocal growth inhibition titers of individual mouse serum with 2 HU of guinea pig complement against Sh.2 cells at the day 24.
[d]Syringe challenge with $10^4$ B. burgdorferi strain Sh.2 was performed at the day 28 (number of mice infected/total tested).
[e]Control mice were injected with solution of 0.1X BSK II in PBS.

Previous studies have shown that there is little detectable antibody response after live cell intradermal immunization with Osp-less cells at a dose that evokes antibodies in animals immunized with Osp-bearing cells. Consequently, to study the immunogenicity of Osp-less cells another immunization approach was needed. Mice were immunized with B311 and 9313 whole cell emulsified in an adjuvant and boosted once with the same preparation. Sera were examined against both immunogens 7 wk after the initial immunization; the results are presented in Table 4. First examined was the immune response by dry ELISA; it was found that reciprocal titers for a homologous reaction were as high as 32,768. When heterologous sera were evaluated, the reciprocal titers were still high: 16,384 for anti-B311 serum against B313 cells, and 4,096 for anti-B313 serum against B311 cells. Sera from mice immunized with CFA alone were negative at a dilution of 1:2. These results confirmed that, besides known Osps, there were other immunogenic components recognized by mice.

Antisera pooled from within the same group were also evaluated by GIA for functional activity (Table 4). To avoid the deleterious effect of complement on Osp-less cells the serum was heat-inactivated. The reciprocal growth inhibitory titer of anti-B311 against B311 was high at 8,192. Anti-B313 serum did not effect B311 cells at any of the dilutions examined. Moreover, Osp-less mutant cells were inhibited by anti-B311 polyclonal serum only at a dilution of 1:32. The latter result, while indicating the specificity of the response, nevertheless, suggested that growth inhibitory antibodies to non-Osp components were produced. This was confirmed by examining the Osp-less mutant cells with homologous anti-B313 serum the reciprocal growth inhibitory titer was 4,096. There was not growth inhibition either B311 or B313 cells by sera of mice immunized with adjuvant and PBS alone.

mAbs Against the Osp-less Mutant

To further characterize the surface antigens of the Osp-less mutant mAbs to B313 were produced. Procedures used for production and screening of hybridoma supernatant fluids were designed to select for and identify those mabs that were directed against surface proteins and had functional activity by GIA. To enhance selection of antibodies against surface components mice were boosted intravenously with live B313 before the spleen fusion. As a screen for surface-directed mAbs, an ELISA was used in which whole borrelias were not dried in the microtiter plate wells. To further evaluate mAbs for surface binding all hybridoma supernatants identified by wet ELISA were examined by unfixed cell immunofluorescence assay. Using these assays several mabs specific for B313 cells were identified.

Figure 1A:
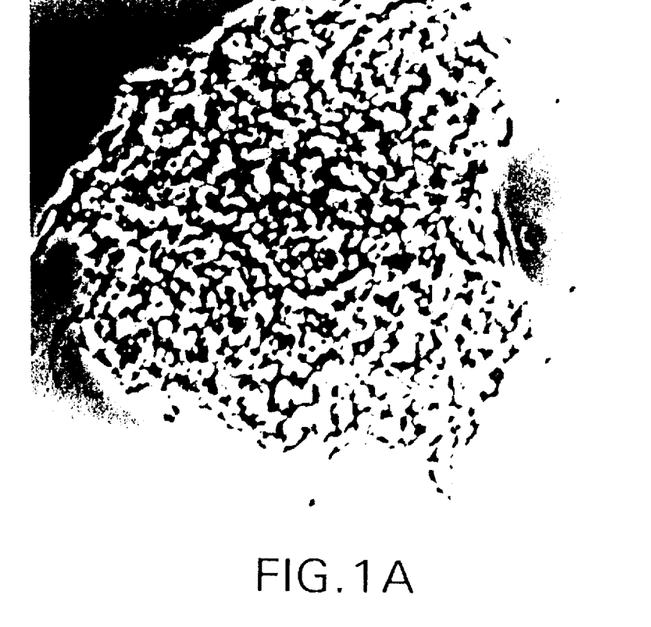
Figure 1B:
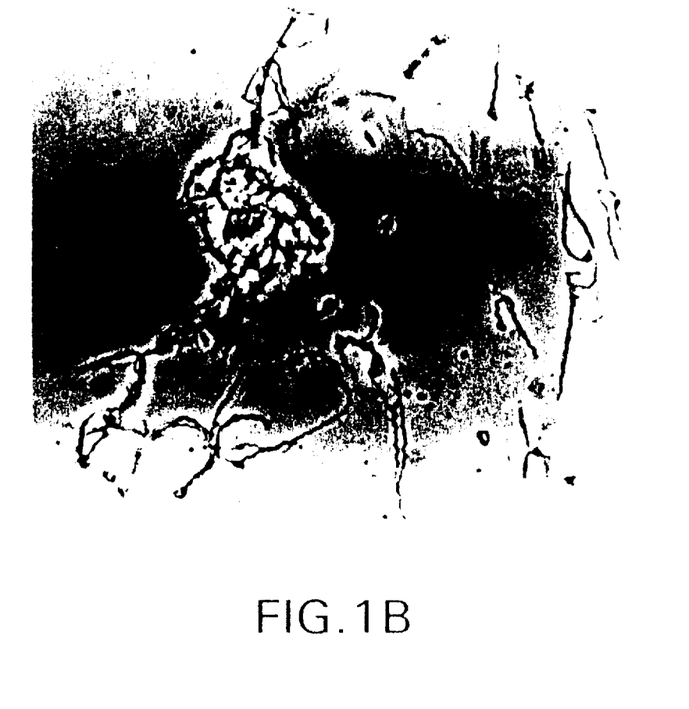

Six mAbs produced against the Osp-less mutant were selected for further study by Western blot and GIA. Two different classes of mAbs were distinguished and designated A and B, in the screening by unfixed cell IFA. The 3 class A mAbs produced prominent cell blebs and 4+ cell aggregates; the 3 class B mAbs produced 3+ aggregates and did not produce blebs (FIG. 1). The morphologic changes observed with class A mabs were similar to what was observed when bactericidal antiborelial antibodies were used (Coleman et al., 1992; Sadziene et al., 1994). Class A mabs were associated with a homogeneous patchy pattern of binding to whole cells and little fluorescent staining of the background.

In contrast class B mAbs in the wet IFA did not produce staining of single whole cells. Instead it was associated with numerous fluorescent spots in the background. By GIA class A antibodies were inhibitory at dilutions of hybridoma supernatant of 1:256–2048; class B mAbs inhibited growth only at dilutions of supernatants of 1;16 or lower. Both class A and B mAbs inhibited the growth of B311 at a dilutions of 1:16 or 1:32, but not at

TABLE 4

ANALYSIS OF POLYCLONAL MOUSE ANTISERA TO B311 AND B313 CELLS BY ELISA AND GROWTH INHIBITION ASSAY[a]

| Polyclonal serum | Mouse No | ELISA[b] | | Growth inhibition assay[c] | |
|---|---|---|---|---|---|
|  |  | B311 | B313 | B311 | B313 |
| Anti-B311 | 1 | 16384 | 16384 | 8192 | 32 |
|  | 2 | 16384 | 16384 |  |  |
|  | 3 | 32768 | 16384 |  |  |
|  | 4 | 32768 | 16384 |  |  |
| Anti-B313 | 1 | 4096 | 16384 | <8 | 4096 |
|  | 2 | 4096 | 16384 |  |  |
|  | 3 | 4096 | 32768 |  |  |
|  | 4 | 2048 | 32768 |  |  |
| Control[d] | 1 | <4 | <4 | <8 | <8 |
|  | 2 | <4 | <4 |  |  |

[a]Mice were immunized with B311 and B313 whole cell emulsion in CFA and were boosted once with the same immunogen.
[b]Reciprocal ELISA titers from individual mouse sera.
[c]Reciprocal growth inhibitory titers of heat-inactivated (56° C., 30 min) pooled mouse sera.
[d]Control mice were immunized with complete Fruend's adjuvant emulsion in PBS.

higher dilutions. None of the antibodies inhibited the growth of B. hermsii. When 1 HU of guinea pig complement was added, it did not increase the inhibitory effect of either class of mAb against B313 cells.

Western Blot Analysis of mAbs

Figure 2:
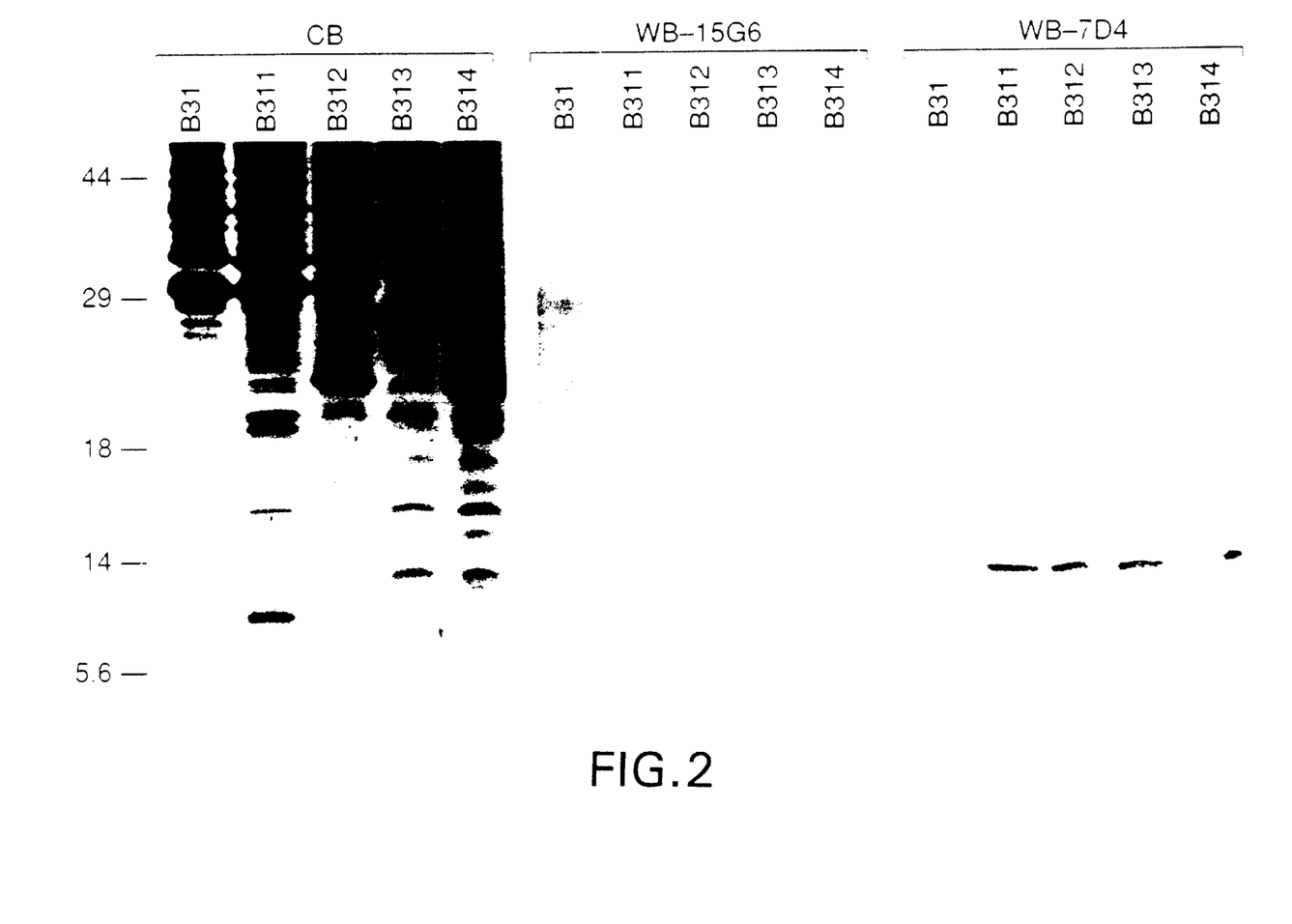

The two classes were also distinguishable by Western Blot. Class B mabs did not bind to any protein in the blots, a result that suggested there mAbs were directed against conformational epitopes or non-proteinaceous antigens. In contrast, all class A mAbs were reactive by Western blot and bound to the same low molecular weight protein. The results with two class A mAbs, 15G6 and 7D4, are shown in FIG.

2. Both these class A mabs were IgG2b. An OspA⁻OspB⁻ *B. burgdorferi* mutant of HB19 lineage has been described that expressed a surface protein not detectable in the Osp-bearing wild-type population (Sadziene et al., 1992). Therefore, it was determined whether or not other lineages of B31 express the protein recognized by 15G6 and 7D4 mAbs. An antibody-reactive protein with an Mr of 13,000 was present in all the B31 cell lineages investigated and in similar amounts. This protein was designated "p13" and was bound by both mabs. Identically-sized proteins bound by 15G6 and 7D4 were present in HB19 and Sh2 strains as well (data not shown). Both mAbs also produced minor bands with proteins with $M_r'$ of 26,000, 32,000, and 44,000 (FIG. 2).

Figure 3A:
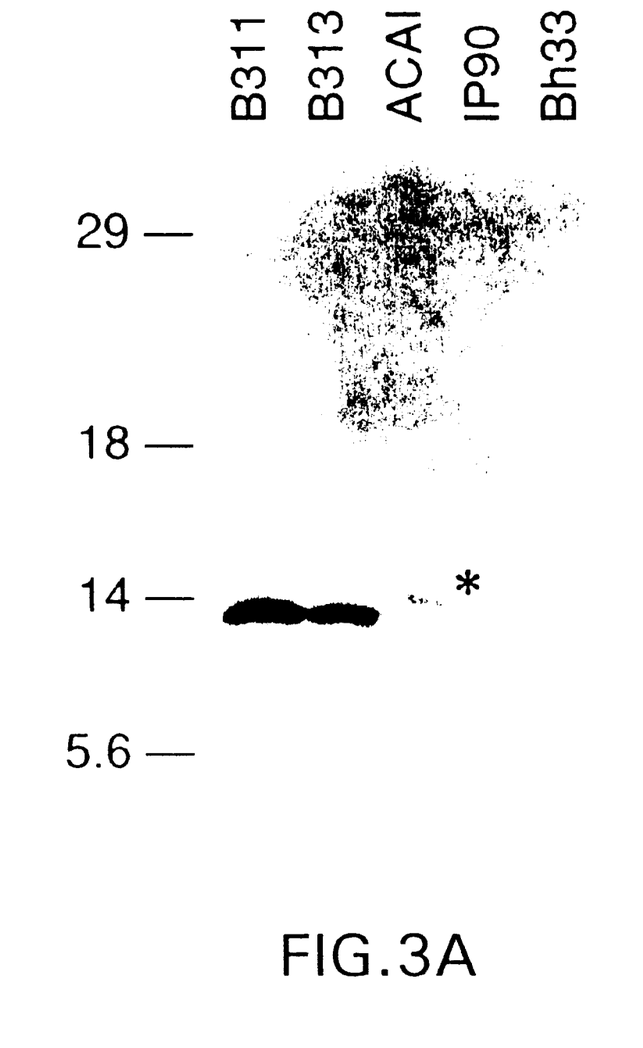
Figure 3B:
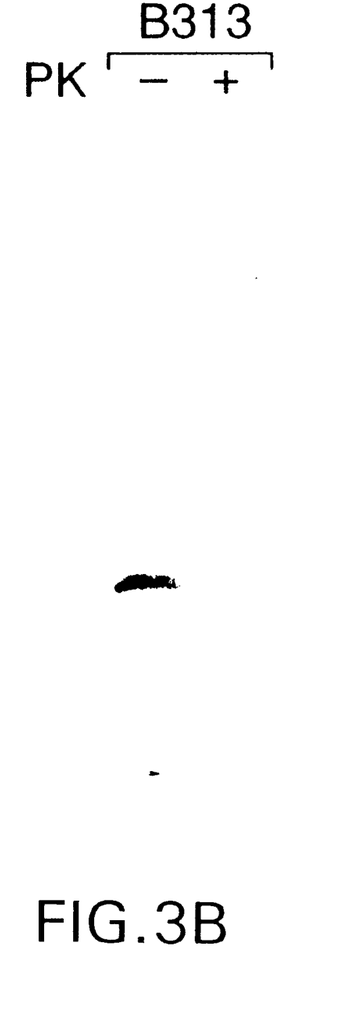

Next, it was determined whether 15G6 or 7D4 mAbs recognized similar or identical proteins in other genomic species of Lyme disease borrelias. The results with 15G6 are shown in FIG. 3; the same results were obtained with 7D4. Representatives of *B. afzelii* and *B. garinii* were evaluated at the same time as B311, B313 and *B. hermsii* cells by Western blot. The mAb recognized a protein of slightly higher apparent molecular weight in *B. afzelii* ACAI. Neither 15G6 nor 7D4 recognized any protein in *B. garinii* IP90 or *B. hermsii*.

It was also investigated whether p13 was cleaved from intact cells by proteinase K, as has been shown for other *B. burgdorferi* surface proteins (Bundoc and Barbour, 1989). No band was observed by Western blot with either anti-p13 kDa mAb after proteinase K digestion of wild-type and Osp-less mutant cells, an indication that p13 is surface-exposed. The result with mAb 15G6 and B313 cells is shown in the right panel of FIG. 3.

Immunofluorescence Studies of p13

To further assess the topography of p13 in the cell, in particular to determine if p13 is exposed over B313's entire surface, fixed and unfixed cells were used in indirect (IFA) and direct (DFA) immunofluorescence assays. Purified 15G6 mAb was used; for unfixed cell DFA purified 15G6 mAb was conjugated with fluorescein.

In the fixed cell IFA B311 and B313 cells were individually mixed with a suspension of washed rat erythrocytes and coated as a thin smear over the slides. No fluorescein-labeled spirochetes were seen with either wild-type or mutant cells when cells were exposed to 15G6 mAb. In contrast, anti-flagellin mAb H9724, used as a control, showed uniform fluorescein labelling of fixed to the glass spirochetes, as described (Barbour et al., 1983). This suggested that the epitope for the 15G6 mAb was sensitive to the experimental conditions and treatment required for the sample preparation. Although this epitope was accessible to 15G6 mAb by the Western blot in the whole-cell lysates, it was not recognized in the dried and fixed borrelias.

Figure 4A:
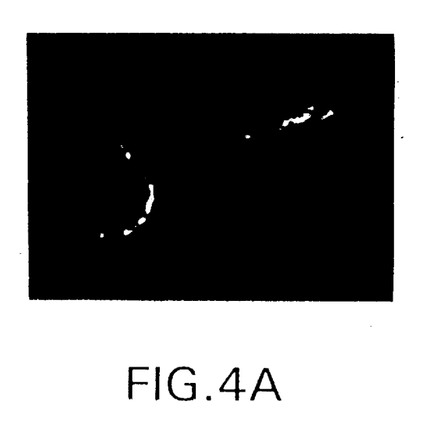
Figure 4B:
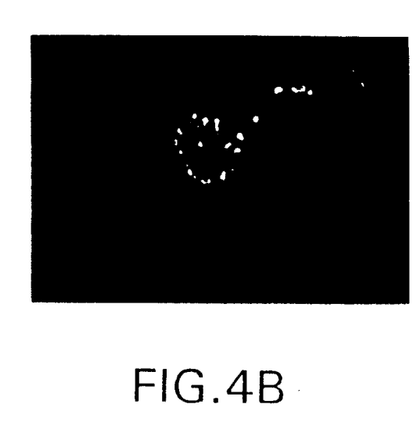
Figure 4C:
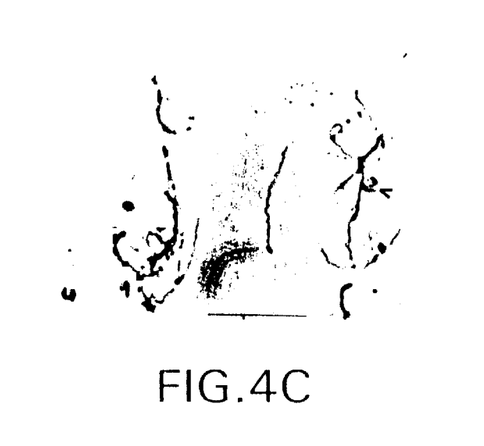
Figure 5A:
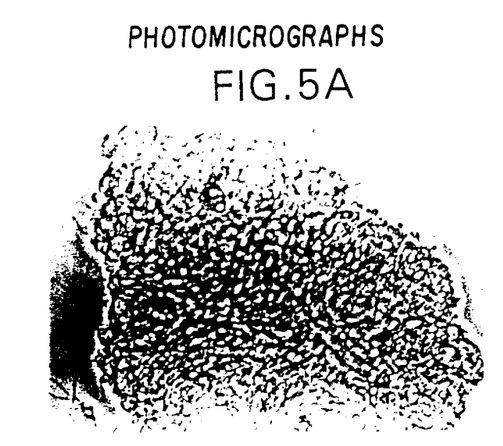
Figure 5B:
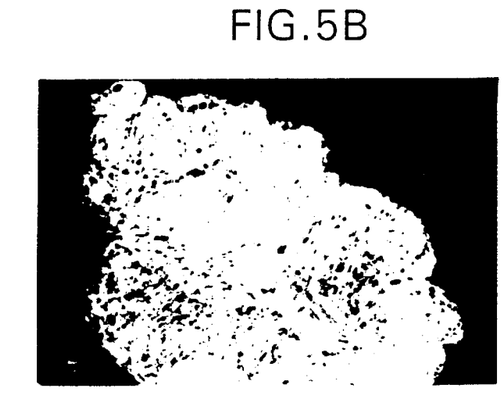
FIGS. 5B and 5D show B311 cells with unconjugated antibody H6831 and conjugated antibody 15G6. 15G6 alone did not bind to B311 cells (not shown). Bar, 2.0 μm.
Figure 5C:
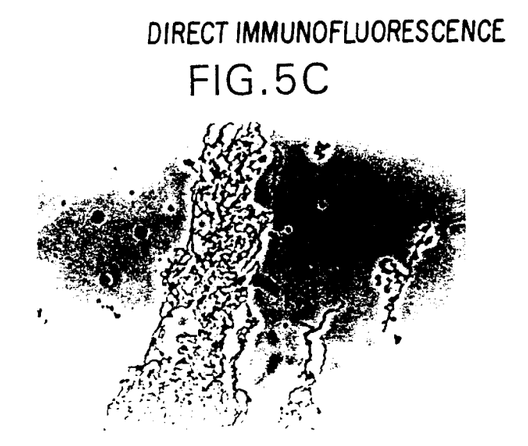
Figure 5D:
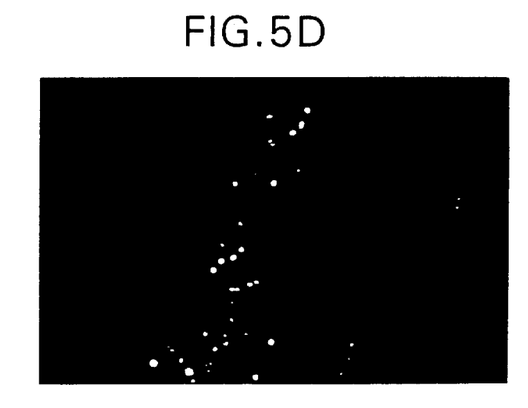

The binding of fluorescein-labeled antibodies to fixed and unfixed borrelias were assessed. B313 cells were examined at 3, 15, 30, 60, and 360 min after addition of the 15G6 conjugate. The cells began to fluoresce within 3 min of addition of the conjugate; the antibody was uniformly distributed over the length of the cell by 30 min (FIG. 4). Cells remained motile for up to 30 min. Cell aggregates and blebs became evident after 15 min and increased in amounts over the 6 hours' observation (FIG. 4). In contrast to B313, very few (<1%) of B311 cells were detectably bound by 15G6 conjugate by DFA with unfixed cells.

The finding that mAb 15G6 had some inhibitory activity against B313 cells, albeit only at a low dilution, suggested that p13 of OspA⁺B⁺ cells was accessible to some degree to the antibody. To determine whether this putative exposure could be increased in wild-type cells by the additional presence of an anti-Osp antibody in the suspension, anti-OspB mAb H6831 or anti-OspA mAb H5332 were used in combination with the 15G6 conjugate. Both antibodies of the combination were added at the same time. The 15G6 conjugate was also used by itself against B311 or B313. Immunofluorescence of cells was examined in 2 h.

As expected the conjugate by itself did not bind to B311 cells when used alone. The conjugate produced aggregation and homogeneous staining of cells of B313 (FIG. 5). In contrast, the binding of the 15G6 conjugate to B311 cells in the presence of the anti-OspA or anti-OspB mAbs was not homogeneous. The results with H6831 and the conjugate are shown in FIG. 5. The cells were found in large aggregates with patches of fluorescence dispersed throughout the clump of cells. The experiment showed that simultaneous exposure to mAbs directed against OspA or OspB resulted in exposure of p13 protein by mAb 15G6.

Functional Characterization of Anti-p13 mAb

Results of these studies prompted further investigation of mAb 15G6 at the functional level, using the whole purified IgG molecule and univalent Fab fragments of 15G6 mAb. Two bactericidal antibodies, anti-OspB mAb H6831 and anti-Bh33 mAb H4825 prepared in the same way served as controls (Sadziene et al., 1994). All mAbs were tested with B311 and B313 cells by GIA (Table 5). As reported previously, the anti-OspB mAb H6831 was highly effective in killing B311 cells but, as expected, produced no damage on the Osp-less mutant cells. The effect of 15 G6 mAb to the Osp-less cells, however, was marked. The MIC of the whole IgG was 20 ng/ml. Univalent fab fragments inhibited growth at a concentration of 200 ng/ml, the same as was observed with the bactericidal Fab fragment directed against Bh33, H4825 (Sadziene et al., 1993C).

As found previously with hybridoma supernatants, 15G6 in purified form inhibited growth of B311 cells only at 25 μg/ml or above. No growth inhibition with either B313 or B311 was observed with the anti-*B. hermsii* mAb H4825. This study proved the functional importance of the newly identified 15G6 mAb to the Osp-less mutant cells and provided evidence that mAbs active as Fab fragments can be produced against other surface proteins besides Osp proteins.

Murine hybridomas secreting monoclonal antibody 15G6 were deposited with the American Type Culture Collection, 10801 University Blvd., Manassas, Va. 20110-2209 under the terms of the Budapest Treaty on Mar. 18, 1999, under Deposit Numbers ATCC IIB-12685 and ATCC IIB-12686.

The combination of anti-Osp and anti-p13 mabs on wild-type cells was further characterized by GIA. Wild-type cells were exposed to two-fold serially diluted purified H6831 (anti-OspB), H5332 (anti-OspA), or, as a control, anti-Bh33 mAb H4825. 15G6 mAb was simultaneously applied at 200 ng/ml, 10× the MIC for B313 and less than 0.01× the MIC for B311. GIA without the addition of mAb 15G6 was performed in parallel. The results are shown in Table 6. There was no effect with mAb H4825, with or without the addition of 15G6 mAb. There was only a two-fold decrease in the MIC of mAb H5332 when mAb 15G6 was added. The effect of the addition of 16G6 to H6831 was more pronounced: without 15G6, its growth inhibitory concentration was 150 ng/ml, whereas with addition of 15G6, intensive cell blebbing occurred at concentrations 64–128-fold lower, i.e., 1–2 ng/ml. These results were consistent with observations of the combination by immunofluorescence assay and indicate that anti-Osp and anti-p13 mAbs are synergistic in their activity against *B. burgdorferi.*

An isolate of *B. burgdorferi* lacking OspA, B, C, and D was characterized with respect to biological functions and its surface antigens, in particular a 13 kDa protein. These results are likely also applicable to other strains of *B. burgdorferi*

TABLE 5

GROWTH INHIBITION BY PURIFIED WHOLE IgG AND Fab FRAGMENTS OF mAbs 15G6, H6831 and H4825 mAbs

| Cells | 15G6 | | H6831 | | H4825 | |
|---|---|---|---|---|---|---|
| | Whole IgG | Fab fragment | Whole IgG | Fab fragment | Whole IgG | Fab fragment |
| B311 | 12.5 | 25 | 0.15 | 2 | >25 | >25 |
| B313 | 0.02 | 0.2 | >25 | >25 | >25 | >25 |

TABLE 6

GROWTH INHIBITION BY PURIFIED WHOLE IgG OF mAbs H6831, H5332, AND H4825 IN COMBINATION WITH mAb 15G6[a]

| | Minimal growth inhibitory concentration (ng/ml) | | |
|---|---|---|---|
| | H6831 | H5332 | H4825 |
| Without 15G6 | 150 | 600 | >25000 |
| With 15G6[a] | 1–2 | 300 | >25000 |

[a]The amount of purified whole IgG of 15G6 mAb was 10X MIC for B313 cells.

sensu lato and the other genomic species of Lyme disease agents. Other isolates of Lyme disease borrelias have one or more of the Osp proteins (reviewed in Barbour and Fish, 1993). The study showed that the Osp-less mutant differed in several ways from the OspAB-bearing parent with which it was compared with. Although the most prominent structural difference between B311 and B313 was their Osp protein phenotypes, differences in other, less abundant proteins or in non-proteinaceous components may have affected changes in function. The most apparent genetic difference between the OspA$^+$B$^+$ B311 and OspA$^-$B$^-$ B313 was the present or absence of the entire 49-kb linear plasmid.

Biological characteristics distinguishing Osp-less and Osp-bearing cells was growth rate and the population density at which stationary phase occurred. Isolate B313 grew more slowly than did B311 and stopped dividing at a lower cell density than did B311. This may be attributable wholly or in part to the greater auto-agglutination displayed by the mutant cells. The triad of self-aggregation, slower growth rate, and lower cell density at stationary phase have also been noted with low-passage, infectious isolates of *B. burgdorferi* (Barbour, 1984; Sadziene et al., 1993C). Like B313, some low-passage isolates of *B. burgdorferi* sensu lato also have a poor plating efficiency on solid medium. The diminished ability of aggregated Osp-less borrelias to move about the broth medium may explain their slower growth under that condition, but why B313 cells could not grow on solid medium when singly dispersed is unknown. Low plating efficiency also is a feature of B314 cells, which lack the 16-kb linear plasmid as well as the 49-kb plasmid (Sadziene et al., 1994). Inasmuch as B314 cells express OspC protein, the lower plating efficiency cannot be attributed to lack of Osp proteins per se.

Curiously, while OspA$^-$B$^-$ cells seem to be inherently more sticky for one another, they were less disposed than OspA$^+$B$^+$ cells to adhere to human endothelial cells. This indicates that the phenomenon of self-aggregation is not equivalent to the association of the borrelias with mammalian cells. Prior studies had revealed functions for OspA in endothelial cell adherence and for OspB in cell penetration (Comstock et al., 1989; Comstock and Thomas, 1991; Thomas and Comstock, 1989). The findings of the present study are also consistent with a role for OspA and/or OspB in the association of borrelias with mammalian cells.

The present invention also examined another possible function of osp proteins, namely resistance to non-immune effects of serum. For a blood-borne pathogen this would seem to be a requirement for successful transmission between hosts and for proliferation within a mammalian host. Much is known about what confers "serum-resistance" to Gram-negative and Gram-positive bacteria; less is known about this aspect of spirochetes. Although borrelias have two membranes sandwiching a peptidoglycan layer, as do Gram-negative bacteria, the outer membrane of borrelias appears to be more fluid than that of Gram-negative bacteria (Barbour and Hayes, 1986) and lack lipid A-containing glycolipids (Takayama et al., 1987). Thus, it was not likely a priori that spirochetes would have a similar mechanism for avoiding the alternative complement pathway and other non-immune defenses against bacteria. Indeed, the results suggest that OspA and/or OspB protect the cells from complement attack. When OspA, B, C, and D are lacking, the borrelias were more susceptible than OspA$^+$B$^+$ cells to unheated, nonimmune serum and to guinea pig complement.

Whatever protection OspA and OspB appeared to confer to the borrelias in serum did not seem to provide an advantage to cells in skin. In these studies two isolates were used that are not infectious by the criterion of detectable dissemination to the blood or other tissues. Surprisingly, the Osp-bearing cells did not survive for a longer period in the skin than did their osp-less counterparts. By 18 hours after inoculation both B311 and B313 could not be recovered from skin samples placed in culture medium. Infectious isolates persist in the skin for days (Barthold et al., 1991). The limited duration of survival noted in the present study may also be a function of inherent strain differences. A non-infectious isolate of strain HB19 of *B. burgdorferi* survived in the skin for 24 hours by the same culture criterion.

Given the indistinguishability of B311 and B313 with respect to skin survival, one might expect that the immune responses to intradermal inoculation of viable borrelias would be comparable. Although the Osp-less mutant lacked two proteins, OspA and OspB, that are immunodominant when syringe inocula of $10^5$ or greater are used (Barthold et al., 1993; Gern et al., 1993; Greene et al., 1988; Roehrig et al., 1992; Schaible et al., 1993), other antigens, such as flagellin, commonly recognized by antibodies in immune sera were still present. Instead, it was found that there was little detectable immune response to *B. burgdorferi* by ELISA, GIA, and infectious challenge when B313 was the immunogen.

Under the same conditions and with the same dose, mice given B311 had high titers to *B. burgdorferi* by immunoassays and were protected against challenge with strain Sh.2. These results suggested that OspA and/or OspB not only are immunodominant antigens but also, perhaps through their mitogenic properties (Ma and Weis, 1993), immunostimulatory.

The present invention also contemplates the possibility that there were no antigens on the cell surface in B313 cells. Without Osp proteins, the cell surface of *B. burgdorferi* conceivably could be like Treponema pallidum's outer membrane, which is notably inert to the immune system (Radolf et al., 1989). To further assess this, mice were immunized with B313 and an adjuvant to enhance immune responsiveness. When this was done, the antiserum produced to B313 cells inhibited the growth of homologous cells but only minimally that of B311. The similar ELISA titers for both anti-B311 and anti-B313 sera against homologous and heterologous cells indicated that with the appropriate adjuvant B313 could elicit antibodies to antigens shared with B311. The GIA results showed that there were unique features of the surface of B313 cells. These components were either not expressed by 311 cells or were otherwise cloaked in these cells.

The minimal effectiveness of polyclonal anti-B311 sera in inhibiting the growth of B313 cells indicated that antibodies to OspA and/or OspB conferred growth inhibition.

The remaining antigens of the Osp-less mutant were further investigated with mAbs. The screening procedures were designed to identify antibodies that had the functional activity of growth inhibition. The antibodies selected by this means fell into two classes: one in which the antibodies in broth medium produced large aggregates and prominent membrane blebs and a second in which the antibodies produced smaller aggregates and minimal evidence of lysis. The first antibodies were found to bind to a 13 kDa (p13) protein in Western blots. The second group of antibodies did not bind to any component in blots. p13 and mAbs to it were therefore characterized in detail.

The evidence that the 13 kDa protein was surface-exposed in the Osp-less mutant was the following: (i) agglutination of viable cells by antibody; (ii) growth inhibition by whole immunoglobulin and Fab fragment; (iii) direct immunofluorescent staining of live cells by an antibody conjugate; and (iv) cleavage of antibody's epitope from the cell's surface by in situ treatment with protease. p13 was present in all members of the B31 lineage and in approximately equal amounts. The expression of the protein did not vary according the amount of one or another the Osp proteins. A slightly larger protein recognized by the mAb was present in a *B. afzelii* strain. If Ip90, a representative of *B. garinii*, have a homologous protein it does not share the mAbs' epitope.

It was considered whether p13 was identical to one of the other low molecular weight *B. burgdorferi* proteins to which antibodies have been developed. Like antibody to p13, antibody to a 10 kDa protein, as reported (Katona et al., 1992), bound to only a small proportion of Osp-bearing cells in immunofluorescence assays. However, the molecular size of 10 kDa protein did not vary between strains and uniform fluorescein labeling was seen in fixed cell preparation when probed with mAb to 10 kDa protein (Katona et al., 1992). Furthermore, 15G6 does not bind to the 10 kDa in Western blots (Habicht, 1993). The presence of a 14 kDa protein of *B. burgdorferi* was reported (Sambri et al., 1991). This was identified with a mAb and by immunofluorescence of live borrelias. In contrast with what was observed with mAbs to p13 and with antibody to the 10 kDa protein (Habicht, 1993), antibody to the 14 kDa protein of Sambri et al. bound to the majority of cells (Sadziene et al., 1993A). These differences suggest that p13 is neither the 10-kDa nor 14-kDa proteins of *B. burgdorferi.*

The effect of 15G6 on susceptible borrelias was similar to what was observed with the anti-OspB mAb H6831 (Sadziene et al., 1994). Binding to the cells was detectable by direct immunofluorescence by 3 minutes. The staining was homogenous and was followed by the appearance of membrane blebs and further cell aggregation even with Fab fragments. The concentration of 15G6 mAb at which growth inhibition and cell disruption occurred was 20 ng/ml. This was 10-fold lower to what was observed with H6381 mAb against *B. burgdorferi* and the same as with H4825 against *B. hermsii* (Sadziene et al., 1993C).

The failure of mAbs to p13 to inhibit the growth of osp-bearing cells is consistent with lack of surface exposure of the protein, or at least impairment of the antibody's access to its target. The cloaking or obstruction could be rom OspA, OspB, or a complex of the two. It was also possible that p13 was not in the outer membrane at all in B311 cells; in those cells it may have been in the periplasmic space or in the cytoplasmic membrane. Evidence against this latter possibility was (i) cleavage of anti-p13 mAbs epitopes from Osp-bearing cells by in situ treatment with proteinase K, (ii) the finding that when mAb 15G6 to p13 was added to antibodies to either OspA or OspB, the growth inhibitory concentration for the anti-Osp antibodies was decreased, substantially with the bactericidal H6831 to OspB.

By itself mAb 15G6 had no discernible effect against B311 cells except at high concentrations. The finding suggested that p13 was exposed to mAb 15G6 when antibodies to OspA or OspB gathered together osp proteins in patches in the fluid outer membrane (Barbour et al., 1983). The immunofluorescence provided visual evidence of this; large membrane blebs of B311 cells treated with anti-OspA or -OspB proteins were bound by conjugated 15G6 mAb. This in vitro synergism between the two antibodies, one directed against an Osp protein and the other against p13, suggests that p13 in combination with OspA or OspB may be useful for immunoprophylaxis against Lyme disease.

These results also provide evidence of the interaction of antibodies and borrelias and, in particular, those lacking the known Osp proteins. The target or targets for the second class of mAbs remains to be determined. It is also possible that they also bind to p13 but that their epitopes are sufficiently conformation-dependent that Western blots would be negative. Alternatively, there may be other proteins or other non-proteinaceous components in the outer membrane against which these functional antibodies act.

REFERENCES

Baranton, G. et al., "Delineation of *Borrelia burgdorferi* sensu stricto, *Borrelia garinii* sp.nov., and group VS461 associated with Lyme borreliosis," *Int. J. Syst. Bacteriol.*, 42:378–383, 1992.

Barbour, A. G., "Immunochemical analysis of Lyme disease spirochetes," *Yale J. Biol. Med.*, 57:581–586, 1984.

Barbour, A. G., "Isolation and cultivation of Lyme disease spirochetes," *Yale J. Biol. Med.*, 57:521–525, 1984.

Barbour, A. G., "Linear DNA or Borrelia species and antigenic variation," *Trends in Microbiology*, 1:236–239, 1993.

Barbour, A. G., "Antibodies of patients with Lyme disease to components of the *Idoxes dammini* spirochete," *J. Clin. Invest.*, 72:504–515, 1983.

Barbour, A. G. and Fish, D., "The biological and social phenomenon of Lyme disease," *Science*, 260:1610–1616, 1993.

Barbour, A. G. and Garon, C. F., "Linear plasmids of the bacterium *Borrelia burgdorferi* have covalently closed ends," *Science*, 237:409–411, 1987.

Barbour, A. G. and Hayes, S. F., "Biology of Borrelia species," *Microbiol. Rev.*, 50:381–400, 1986.

Barbour, A. G. et al., "A Borrelia-specific monoclonal antibody binds to a flagellar epitope," *Infect. Immun.*, 52:549–554, 1986.

Barbour, A. G. et al., "Variation in a major surface protein of Lyme disease spirochetes," *Infect. Immun.*, 45:94–100, 1984.

Barbour, A. G. et al., "Variable major proteins of *Borrelia hermsii*," *J. Exp. Med.*, 156:1312–1324, 1982.

Barbour, A. G. et al., "Lyme disease spirochetes and Ixodes tick spirochetes share a common surface antigen determinant defined by a monoclonal antibody," *Infect. Immun.*, 41:795–804, 1983.

Barthold, S. W. and Bockenstedt, L. K., "Passive immunizing activity of sera from mice infected with *Borrelia burgdorferi*," *Infect. Immun.*, 61:4696–4702, 1993.

Barthold, S. W. et al., "Kinetics of *Borrelia burgdorferi* dissemination and evolution of disease after intradermal inoculation of mice," *Am. J. Pathol.*, 139:263–272, 1991.

Benach, J. L. et al., "Biological activity of *Borrelia burgdorferi* antigens," *Ann. NY Acad. Sci.*, 539:115–125, 1988.

Bergstrom, S. et al., "Molecular analysis of linear plasmid-encoded major surface proteins, OspA and OspB, of the Lyme disease spirochaete *Borrelia burgdorferi*," *Mol. Microbiol.*, 3:479–486, 1989.

Boerlin, P. et al., "Population genetic analysis of *Borrelia burgdorferi* isolates by multilocus enzyme electrophoresis," *Infect. Immun.*, 60:1677–1683, 1992.

Boyd, R. F. and Hoerl, B. G., "Nonspecific host resistant factors, p. 321–333, In B. A. C. Little (ed.), Basic Medical Microbiology, Boston/Toronto.

Brandt, M. E. et al., "Immunogenic integral membrane proteins of *Borrelia burgdorferi* are lipoproteins," *Infect. Immun.*, 58:983–991, 1990.

Brusca, J. S. et al., "Localization of outer surface proteins A and B in both the outer membrane and intracellular compartments of *Borrelia burgdorferi*," *J. Bacteriol.*, 173:800408, 1991.

Bundoc, V. G. and Barbour, A. G., "Clonal polymorphisms of outer membrane protein OspB of *Borrelia burgdorferi*," *Infect. Immun.*, 57:2733–2741, 1989.

Burgdorfer, W. et al., "Lyme disease-A tick-borne spirochetosis?," *Science*, 216:1317–1319, 1982.

Cadavid, D. et al., "Variability of a bacterial surface protein and disease expression in a possible mouse model of systemic Lyme borreliosis," *J. Exp. Med.*, 179:631–642, 1994.

Canica, M. M. et al., "Monoclonal antibodies for identification of *Borrelia afzelii* sp.nov. associated with late cutaneous manifestations of Lyme borreliosis," *Scand. J. Infect. Dis.*, 25:441–448, 1993.

Coleman, J. L. et al., "Selection of an escape variant of *Borrelia burgdorferi* by use of bactericidal monoclonal antibodies to OspB," *Infect. Immun.*, 60:3098–3104, 1992.

Comstock, L. E., "Monoclonal antibody to OspA inhibits association of *Borrelia burgdorferi* with human endothelial cells," *Infect. Immun.*, 61:423–431, 1992.

Comstock, L. E. and Thomas, D. D., "Penetration of endothelial cell monolayers by *Borrelia burgdorferi*," *Infect. Immun.*, 57:1626–1628, 1989.

Comstock, L. E. and Thomas, D. D., "Characterization of *Borrelia burgdorferi* invasion of cultured endothelial cells," *Microbiol. Pathogen*, 10:137–148, 1991.

Gern, L. et al., "Mode of inoculation of the Lyme disease agent *Borrelia burgdorferi* influences infection and immune responses in inbred strains of mice," *J. Infect. Dis.*, 167:971–976, 1993.

Greene, R. T. et al., "Immunoblot analysis of Immunoglobulin G response to the Lyme disease agent (*Borrelia burgdorferi*) in experimentally and naturally exposed dogs," *J. Clin. Microbiol.*, 648:648–653, 1988.

Habicht, G., Personal communication, 1993.

Hinnebush, J. and Barbour, A. G., "Linear- and circular-plasmid copy numbers in *Borrelia burgdorferi*," *J. Bacteriol.*, 174:5251–5257, 1992.

Holt, S. C., "Anatomy ad chemistry of spirochetes," *Microbiol. Rev.*, 38:114–160, 1978.

Howe, T. R. et al., "A single recombinant plasmid expressing two major outlet surface proteins of the Lyme disease spirochete," *Science*, 227:645–646, 1985.

Jonsson, M. et al., "Heterogeneity of outer membrane proteins in *Borrelia burgdorferi*: comparison of osp operons of three isolates of different geographic origins," *Infect. Immun.*, 60:1845–1853, 1992.

Katona, L. I. et al., "Purification and immunological characterization of a major low-molecular-weight lipoprotein from *Borrelia burgdorferi*," *Infect. Immun.*, 60:4995–5003, 1992.

Kitten, T. and Barbour, A. G., "Juxtaposition of expressed variable antigen genes with a conserved telomere in the bacterium *Borrelia hermsii*," *Proc. Natl. Acad. Sci. USA*, 87:6077–6081, 1990.

Kochi, S. K. and Johnson, R. C., "Role of immunoglobulin G in killing of *Borrelia burgdorferi* by the classical complement pathway," *Infect. Immun.*, 56:314–321, 1987.

Lam, T. T. et al., "Outer surface proteins E and F or *Borrelia burgdorferi*, the agent of Lyme disease," *Infect. Immun.*, 62:290–298, 1994.

Luft, B. J. et al., "Biochemical and immunochemical characterization of the surface proteins of *Borrelia burgdorferi*, *Infect. Immun.*, 57:3637–3645, 1989.

Ma, Y. and Weiss, J. J., "*Borrelia burgdorferi* outer surface lipoproteins OspA and OspB possess B-cell mitogenic and cytokine-stimulatory properties," *Infect. Immun.*, 61:3843–3853, 1993.

Meier, J. et al., "Antigenic variation is associated with DNA rearrangement in a relapsing fever borrelia," *Cell*, 41:403–407, 1985.

Norris, S. J. et al., "Low passage-associated proteins of *Borrelia burgdorferi*: characterization and molecular cloning of OspD, a surface-exposed, plasmid-encoded lipoprotein," *Infect. Immun.*, 60:4662–4672, 1992.

Oi, V. T. and Herzenberg, L. A., "Immunoglobulin-producing hybrid cell lines," p. 351–372, In B.B.M.a.S.M. Shiigis (ed.), Selected Methods in Cellular Immunology, W.H. Freeman and Co., San Francisco, 1980.

Radolf, J. D. et al., "Outer membrane ultrastructure explains the limited antigenicity of virulent *Treponema pallidum*," *Proc. Natl. Acad. Sci. USA*, 86:2051–2055, 1989.

Roehrig, J. T. et al., "The hamster immun response to tick-transmitted *Borrelia burgdorferi* differs from the response to needle-inoculated, cultured organisms," *J. Immunol.*, 149:3648–3653, 1992.

Sadziene, A. et al., "An OspB mutant of *Borrelia burgdorferi* has reduced invasiveness in vitro and reduced infectivity in vivo," *Infect. Immun.*, 61:3590–3596, 1993A.

Sadziene, A. et al., "A bactericidal antibody to *Borrelia burgdorferi* is directed against a variable region of the OspB protein," *Infect. Immun.*, in press, 1994.

Sadziene, A. et al., "Antibody-resistant mutants of *Borrelia burgdorferi*: in vitro selection and characterization," *J. Exp. Med.*, 176:799–809, 1992.

Sadziene, A. et al., "A flagella-less mutant of *Borrelia burgdorferi*," *J. Clin. Invest.*, 88:82–92, 1991.

Sadziene, A. et al., "In vitro inhibition of *Borrelia burgdorferi* growth by antibodies," *J. Infect. Dis.*, 167:165–172, 1993C.

Sadziene, A. et al., "The cryptic OspC gene of *Borrelia burgdorferi* B31 is located on a circular plasmid," *Infect. Immun.*, in press, 1993B.

Sambri, V. et al., "Immunological characterization of a low molecular mass polypeptidic antigen of *Borrelia burgdorferi*," *FEMS Microb. Immunol.*, 76:345–350, 1991.

Schaible, U. E. et al., "Distinct patterns of protective antibodies are generated against *Borrelia burgdorferi* in mice experimentally inoculated wit high and low doses of antigen," *Immunology Letters*, 36:219–226, 1993.

Schwan, T. G. et al., "Changes in infectivity and plasmid profile of the Lyme disease spirochete, *Borrelia burgdorferi*, as a result of in vitro cultivation," *Infect. Immun.*, 56:1831–1836, 1988.

Simpson, W. J. et al., "Antibody to a 39-kilodalton *Borrelia burgdorferi* antigen (P39) as a marker for infection in experimentally and naturally inoculated animals," *J. Clin. Microbiol.*, 29:236–243, 1991.

Steere, A. C., "Lyme disease," *New Engl. J. Med.*, 321:586–596, 1989.

Steere, A. C. et al., "The spirochetal etiology of Lyme disease," *New Engl. J. Med.*, 308:733–740, 1983.

Takayama, K. et al., "Absence of lipopolysaccharide in the Lyme disease spirochete, *Borrelia burgdorferi*," *Infect. Immun.*, 55:2311–2313, 1987.

Thomas, D. D. and Comstock, L. E., "Interaction of Lyme disease spirochetes with cultured eucaryotic cells," *Infect. Immun.*, 57:1324–1326, 1989.

Welsh, J. et al., "Genomic fingerprinting by arbitrarily primed polymerase chain reaction resolves *Borrelia burgdorferi* into three distinct phyletic groups," *Int. J. Syst. Bacteriol.*, 42:370–377, 1992.

Wilske, B. et al., "Immunological and molecular polymorphism of OspC: an immunodominant major outer surface protein of *Borrelia burgdorferi*," *Infect. Immun.*, 61:2182–2191, 1993.

The above references, to the extent that they provide exemplary procedural or other details supplementary to those set forth herein, are all specifically incorporated herein by reference.

What is claimed is:

1. A protein composition, consisting essentially of an isolated protein having a molecular weight of about 13 kDa as determined by sodium dodecyl sulfate polyacrylamide gel electrophoresis (SDS/PAGE), that binds to the monoclonal antibody 15G6 and is isolatable from *Borrelia burgdorferi*.

2. The protein composition of claim 1, wherein the comnposition further consists essentially of *Borrelia burgdorferi* outer membrane proteins OspA, OspB, OspC or OspD.

3. An isolated protein having the following characteristics:
   (a) isolatable from *Borrelia burgdorferi*;
   (b) present on the surface of *Borrelia burgdorferi* cells that lack the outer membrane proteins OspA, OspB, OspC and OspD;
   (c) sensitive to cleavage with proteinase K;
   (d) a molecular weight of about 13 kDa, as determined by SDS/PAGE; and
   (e) binding to monoclonal antibody 15G6.

4. The isolated protein of claim 3, further defined as being obtained from *Borrelia burgdorferi* cells.

5. An isolated protein characterized as: isolatable from *Borrelia burgdorferi*; having a molecular weight of about 13 kDa, as determined by SDS/PAGE; and binding to monoclonal antibody 15G6.

6. The isolated protein of claim 5, linked to a detectable label.

7. The isolated protein of claim 3, linked to a detectable label, the label being a radioactive label, a Flourogenic label, a nuclear magnetic spin resonance label, biotin or an enzyme that generates a colored product upon contact with a chromogenic substrate.

8. A method for detecting antibodies to *Borrelia burgdorferi* comprising contacting a sample suspected of containing antibodies to *Borrelia burgdorferi* with a protein as claimed in claim 5 under antibody-binding conditions and detecting any antibody binding to the protein, whereby antibody binding to the protein is indicative of the presence of antibodies to *Borrelia burgdorferi*.

9. A method for inducing an immunological response comprising administering to an animal a pharmaceutically acceptable composition comprising the protein of claim 5.

10. The method of claim 9 wherein the pharmaceutically acceptable comnposition further comprises *Borrelia burgdorferi* OspA, OspB, OspC or OspD.

* * * * *

UNITED STATES PATENT AND TRADEMARK OFFICE
CERTIFICATE OF CORRECTION

PATENT NO. : 6,300,101 B1
DATED : October 9, 2001
INVENTOR(S) : Sadziene et al.

It is certified that error appears in the above-identified patent and that said Letters Patent is hereby corrected as shown below:

Column 1,
After line 12, insert:
-- STATEMENT REGARDING FEDERALLY SPONSORED RESEARCH
 This invention was made in part with support from the Federal government through NIH Grants Nos. AI-29731 and AI-26804. The Federal government has certain rights in the invention. --

Signed and Sealed this

Fourth Day of June, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,300,101 B1
DATED        : October 9, 2001
INVENTOR(S)  : Ariadna Sadziene and Alan G. Barbour It is certified that error appears in the above-identified patent and that said Letters Patent is hereby corrected as shown below:

Title page,
Item [63], please change "Continuation-in-part of application No. 08/079,601, filed on Jun. 22, 1992, now Pat. No. 5,523,089, which is a continuation of application No. 07/924,798, filed on Aug. 6, 1992, now abandoned, which is a continuation of application No. 07/422,881, filed on Oct. 18, 1989, now abandoned."
to -- Continuation-in-part of application No. 08/079,601, filed on Jun. 22, 1992, now Pat. No. 5,523,089, which is a continuation of application No. 07/924,798, filed on Aug. 6, 1992, now abandoned, which is a continuation of application No. 07/422,881, filed on Oct. 18, 1989, now abandoned. This application is also a continuation-in-part of application No. 08,124,771, which is a continuation-in-part of application No. 07/781,355, filed October 22, 1991, now Pat. No. 5,246,844. --.

Signed and Sealed this

Eighteenth Day of November, 2003

JAMES E. ROGAN
*Director of the United States Patent and Trademark Office*